United States Patent
White

(10) Patent No.: US 9,327,998 B2
(45) Date of Patent: May 3, 2016

(54) PHOTOINHIBITION OF MICROBIAL NITRIFICATION IN POTABLE WATER

(71) Applicant: Department of Water and Power of the City of Los Angeles, Los Angeles, CA (US)

(72) Inventor: Brian Nelson White, Los Alamitos, CA (US)

(73) Assignee: Department of Water and Power of the City of Los Angeles, Los Angeles, CA (US)

( * ) Notice: Subject to any disclaimer, the term of this patent is extended or adjusted under 35 U.S.C. 154(b) by 0 days.

(21) Appl. No.: 14/010,448

(22) Filed: Aug. 26, 2013

(65) Prior Publication Data

US 2014/0054240 A1    Feb. 27, 2014

Related U.S. Application Data

(63) Continuation of application No. 12/879,844, filed on Sep. 10, 2010, now abandoned.

(51) Int. Cl.
    *C02F 1/30*     (2006.01)
    *C12N 13/00*     (2006.01)

(52) U.S. Cl.
    CPC .. *C02F 1/30* (2013.01); *C12N 13/00* (2013.01)

(58) Field of Classification Search
    CPC ............. A61L 2/08; A61L 2/084; A61L 2/10; C12N 13/00; C02F 1/30
    USPC ......................................................... 422/292
    See application file for complete search history.

(56) References Cited

U.S. PATENT DOCUMENTS 3,649,493 A  *  3/1972   Meiners et al. ............ 204/157.5

* cited by examiner

*Primary Examiner* — Sean E Conley
(74) *Attorney, Agent, or Firm* — Lewis Roca Rothgerber Christie LLP

(57) ABSTRACT

A method for providing a dose of visible light in covered drinking water storage facilities to control nitrification. In one embodiment, the method includes irradiating the water with a dose of visible light sufficient to inhibit microbial nitrification of the water. In one embodiment, the dose of visible light has a wavelength from approximately 400 Hz to approximately 700 Hz. In another embodiment, the dose of visible light has a wavelength from approximately 550 Hz to approximately 700 Hz. In a further embodiment, the dose of visible light has a wavelength from approximately 380 Hz to approximately 430 Hz.

7 Claims, 11 Drawing Sheets

US 9,327,998 B2

PHOTOINHIBITION OF MICROBIAL NITRIFICATION IN POTABLE WATER

CROSS-REFERENCE TO RELATED APPLICATION(S)

This application is a continuation and claims priority to and the benefit of U.S. patent application Ser. No. 12/879,844, filed Sep. 10, 2012, the entire contents of which are hereby incorporated by reference.

BACKGROUND

The present invention generally relates to apparatus and methods for controlling microbial nitrification and more specifically, to apparatus and methods for providing a dose of ultraviolet-A (UVA)/Visible light in covered drinking water storage facilities to control nitrification.

It is well established in the scientific literature that the enzymes used by nitrifying microbes to first oxidize ammonia to nitrite and then nitrite to nitrate are inhibited by UVA and visible light. Potable water is often stored in large water storage tanks. Nitrifying microbes may produce nitrites and nitrates through the oxidation of ammonia produced by the degradation of chloramine disinfectant.

In covered drinking water storage, nitrification contributes to the loss of disinfectant residual, stimulates the growth of other nuisance microbes and produces nitrite and nitrate, both of which are regulated drinking water contaminants. Nitrate is the cause of methemoglobinemia (blue-baby syndrome) in infants.

SUMMARY

In one aspect of the present invention, a system for the photoinhibition of microbial nitrification of potable drinking water comprises a tank for holding water; and at least one lamp irradiating light into the water.

These and other features, aspects and advantages of the present invention will become better understood with reference to the following drawings, description and claims.

BRIEF DESCRIPTION OF THE DRAWINGS

Apparatuses and methods for inhibiting microbial nitrification according to various embodiments of the present disclosure are described with reference to the following figures. The same reference numerals are used throughout the figures to reference like features and components. The figures are not necessarily drawn to scale.

DETAILED DESCRIPTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, embodiments of the present invention generally provide an inhibiting dose of UVA/Visible light in covered drinking water storage facilities to prevent nitrification. Embodiments of the current invention use UVA/Visible radiation to control bacterial nitrification in an industrial setting.

As used herein, an "inhibiting dose" of UVA/Visible light may be radiation at a suitable wavelength and intensity over a specific period of time, typically 24 hours or less, to inhibit enzymes used in nitrifying microbes. For example, an inhibiting dose may be radiation having a wavelength between 315 and 430 nanometers (nm) and an incident irradiance of at least 0.01 watts per square meter (W/m2) over a period of 24 hours, typically at least 0.01 W/m2.

As used herein, the term "photo-inhibition", with respect to microbial nitrification, refers to not only the prevention of microbial nitrification in water, but also to the treatment of microbial nitrification once such a process has started. Similarly, "reducing" microbial nitrification of water refers not only to lessening the rate and/or degree of microbial nitrification, but also to the elimination of microbial nitrification of water.

Figure 1:
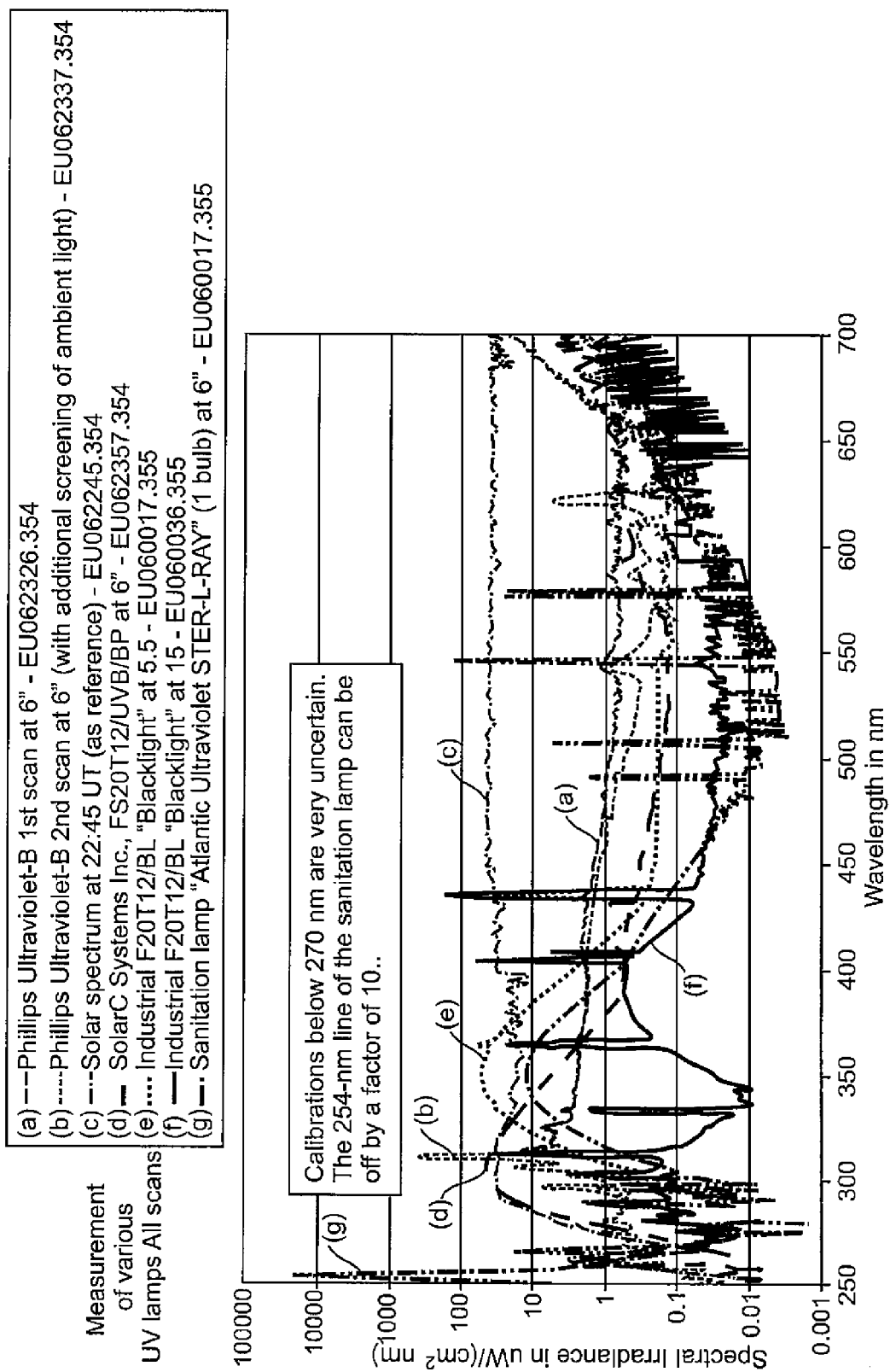
FIG. 1 is a graph of incident irradiance over a spectrum between 250 and 700 nm for a variety of lamps.

Referring to FIG. 1, there is shown a graph of incident irradiance over a spectrum between 250 and 700 nm for a variety of lamps. After several tests and exploration of a variety of lamps, a blue-blocking blacklight lamp was chosen as the lamp to use in the below described experiments. While this specific lamp was chosen for further study, the invention should not be limited to any particular lamp, provided that the lamp may provide an adequate dose to achieve the desired result of inhibiting microbial nitrification. For example, fluorescent, incandescent or LED lamps may be useful in various embodiments of the present invention.

Figure 2:
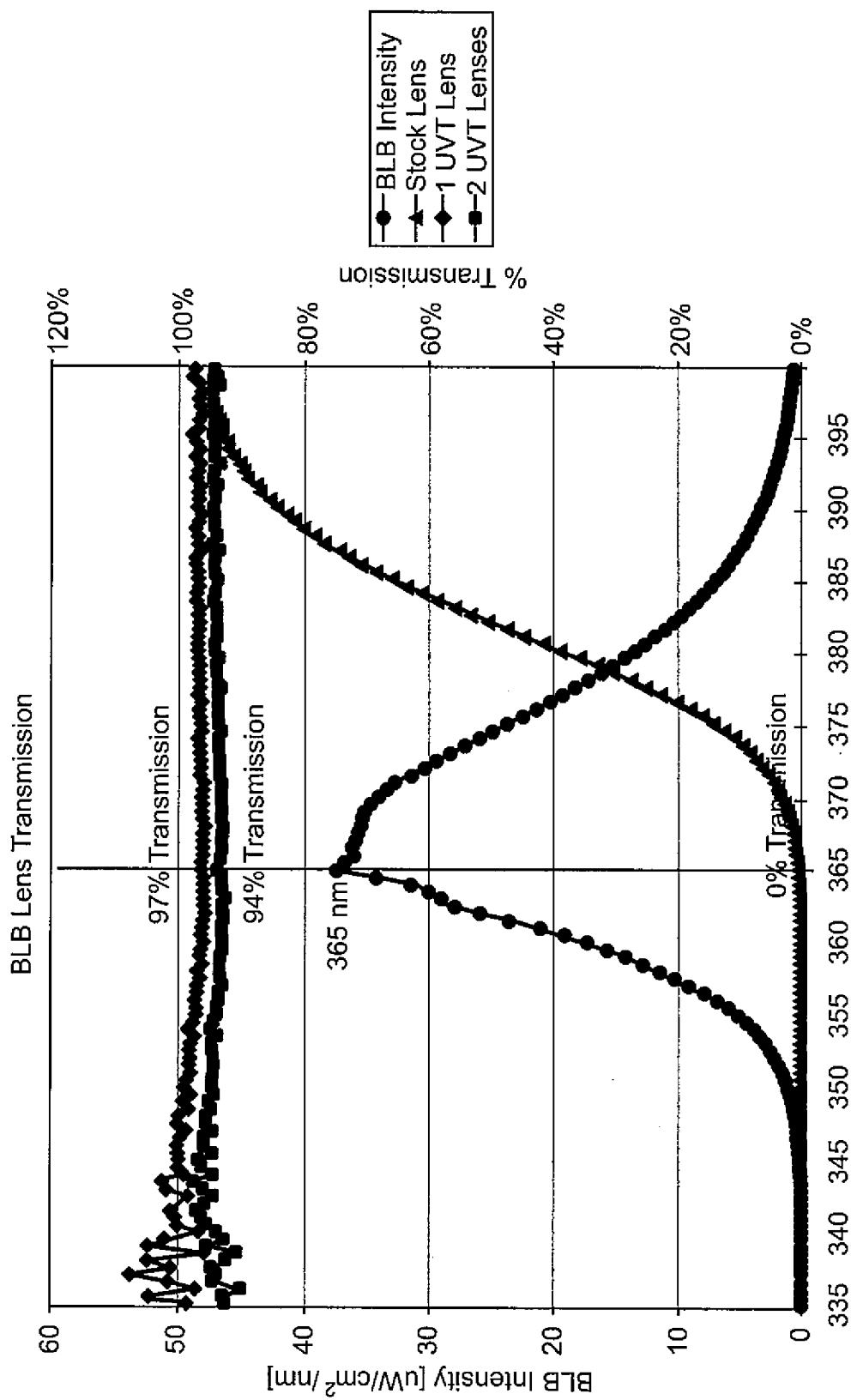
FIG. 2 a graph showing the incident irradiance of an exemplary blue-blocking blacklight lamp (BLB) through various lenses.

Referring to FIG. 2, there is shown a graph of the irradiance of an exemplary blue-blocking blacklight lamp (BLB) through various lenses. In this graph, the emission spectrum of the BLB lamp is shown by the line with the circles. This line should be read against the Y-axis on the left. The other three lines show the percent transmission of the BLB emission spectrum through various lenses—a stock lens (triangle-marked line), a UVA transmitting lens (diamond-marked line), and two stacked UVA transmitting lenses (square-marked line). As can be seen, the UVA transmitting lenses provided a greater transmittance throughout the entire measured spectrum (335-400 nm).

Figure 3:
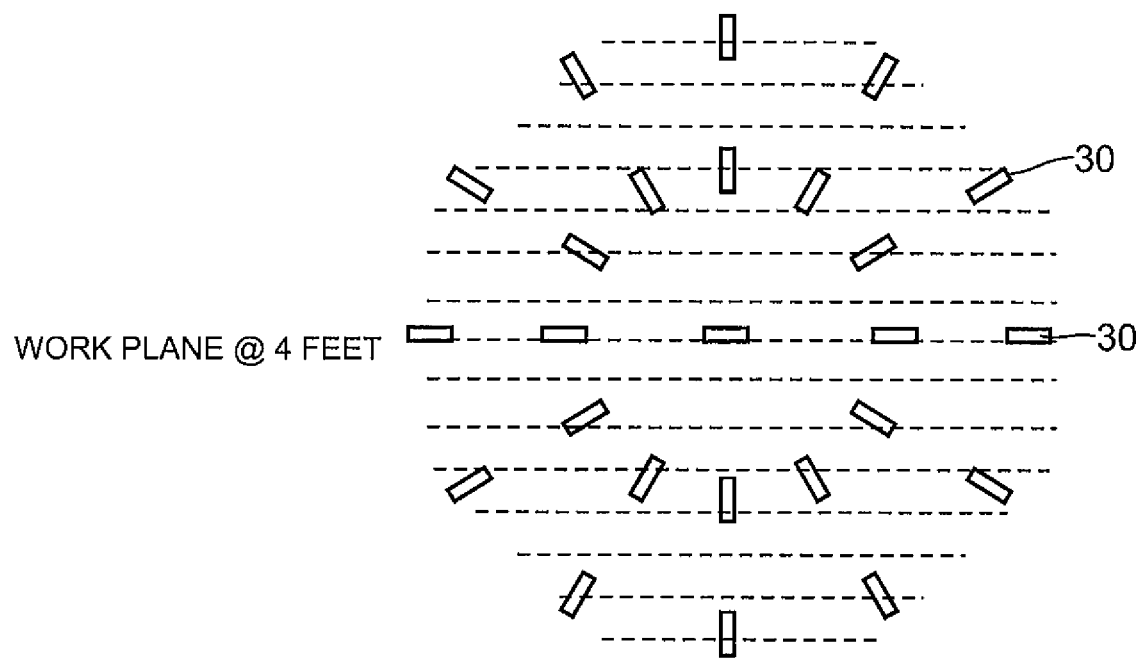
FIG. 3 shows a lighting design according to an embodiment of the present invention.

Referring now to FIG. 3, there is shown a lighting design useful in a water storage tank, according to an embodiment of the present invention. The lighting design uses a number of light banks 30, each containing at least one lamp, such as at least one F40T12BLB median bipin fluorescent lamp (not shown). The exemplary lighting design of FIG. 3 may be based on comparative scans of warm white lamps with suitable design software. The lighting design of FIG. 3 should be taken as an exemplary lighting design and should not be considered as limiting the choice of lighting design useful in the present invention.

Figure 4:
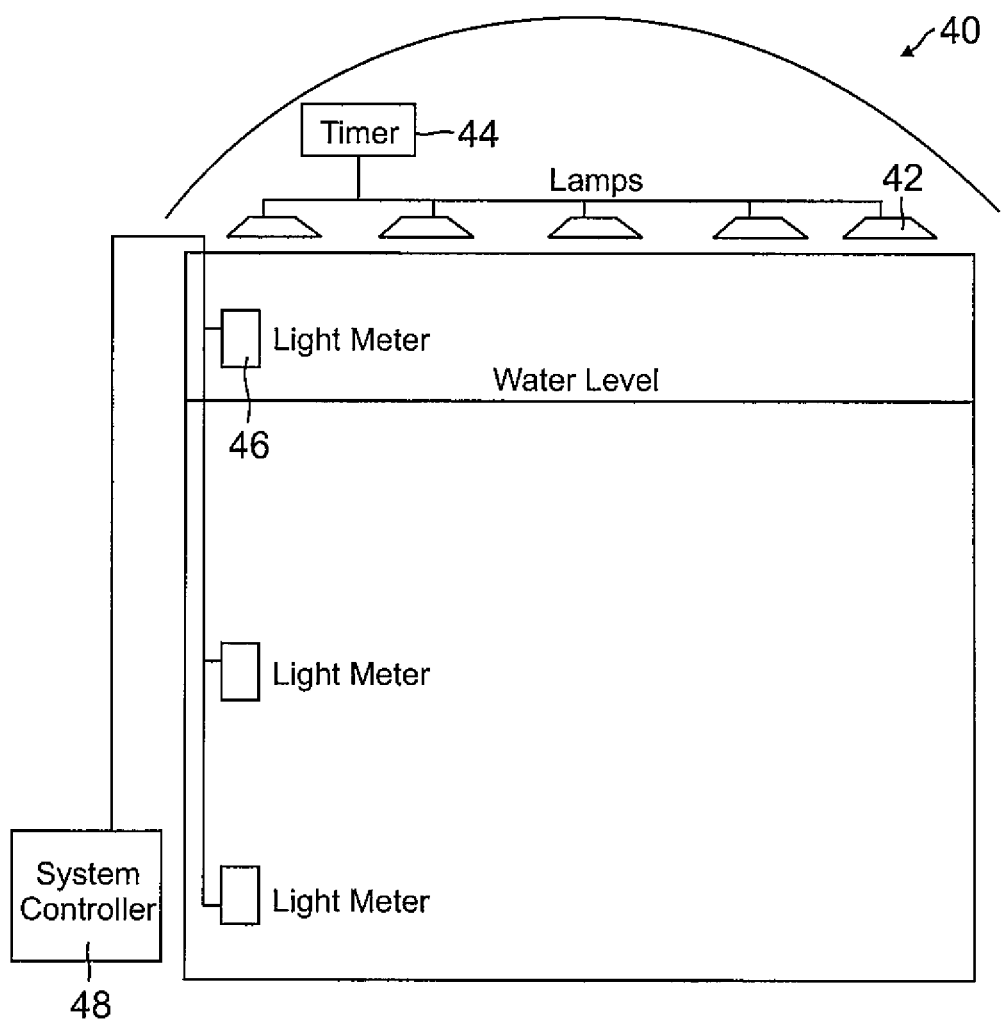
FIG. 4 is a schematic drawing of a water storage tank having a microbial nitrification photo-inhibition system according to an exemplary embodiment of the present invention.

Referring to FIG. 4, there is shown a schematic drawing of a water storage tank 40 having a microbial nitrification photo-inhibition system according to the present invention. The system may include a plurality of lamps 42, such as the BLB lamps as described above. The lamps may be controlled by a timer 44. The output of the lamps 42 may be measured by at least one light meter 46. Typically, a number of light meters 46 may be disposed at various locations above ground level (AGL). For example, as shown in FIG. 4, three light meters 46 may be disposed along one side of the water storage tank 40. While the lamps 42 are shown above the water level, the lamps 42 may be located at various locations inside the water tank 40, such as above the water level, submerged in the water within the tank 40, or floating on top of the water in the tank 40.

Figure 5:
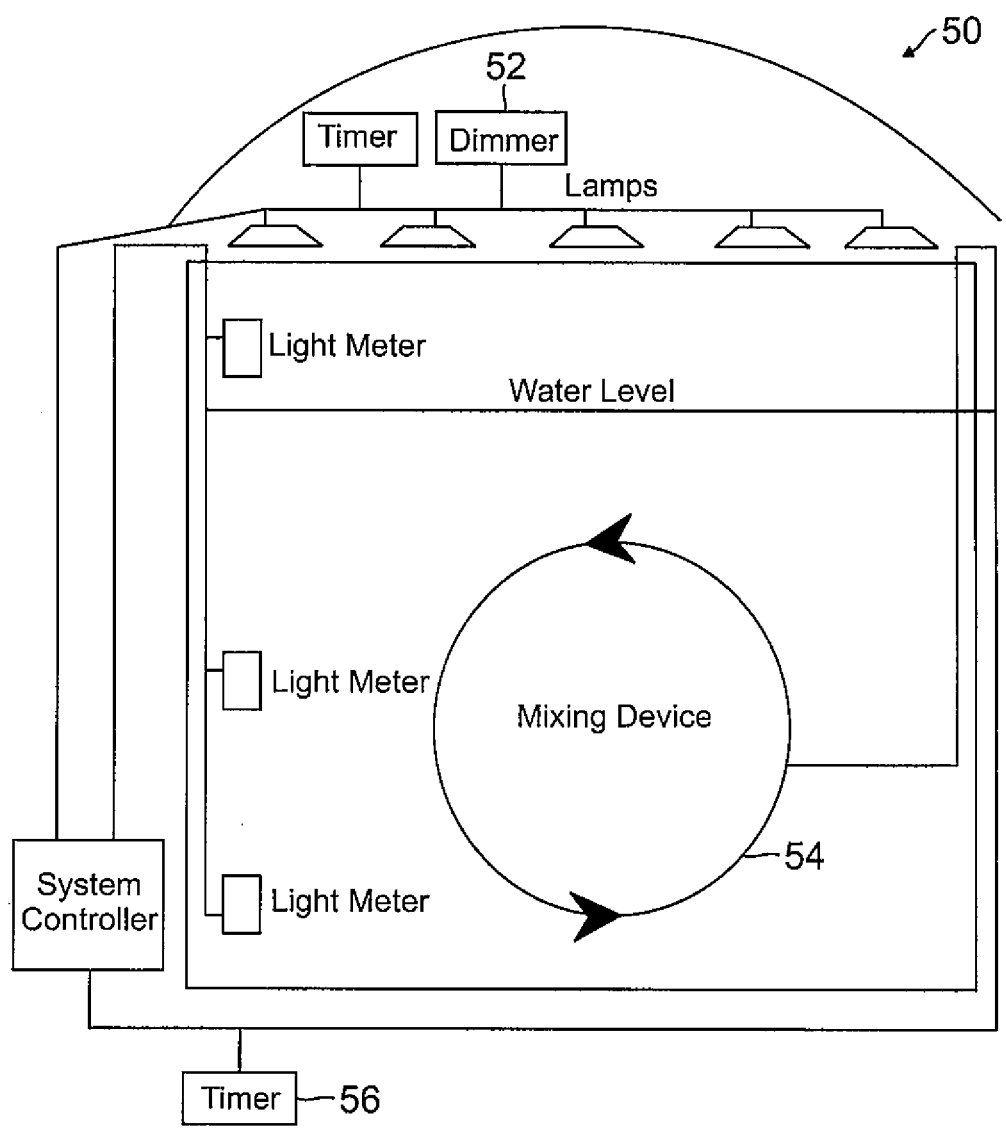
FIG. 5 is a schematic drawing of a water storage tank having a microbial nitrification photo-inhibition system according to an alternate exemplary embodiment of the present invention.

In one exemplary embodiment of the present invention, as shown in FIG. 5, a water storage tank 50 may be similar to the water storage 40 described above, with the addition of a dimmer 52 for controlling the intensity of the output of the lamps. The water storage tank 50 may also include a mixing device 54 for mixing water stored in the tank 50. The mixing device 54 may be controlled by a timer 56. Control of the various components, such as the lamps, timers, dimmers, mixing devices and the like may be performed on-site or remotely via any known control technique. For example, a Supervisory Control and Data Acquisition (SCADA) system may be used to remotely control the system of the present invention.

Figure 6:
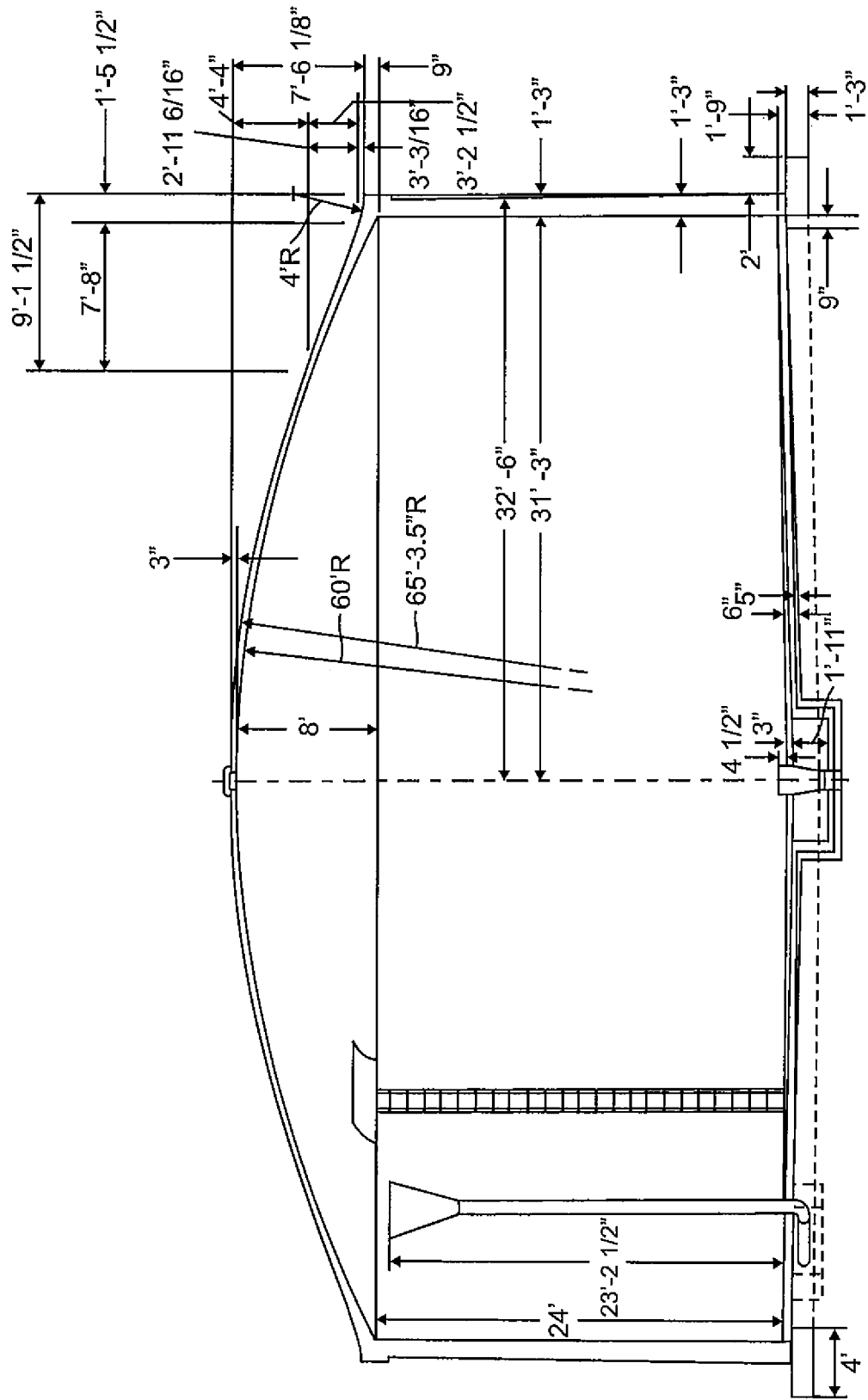
FIG. 6 is an engineering drawing of an exemplary storage tank used in the various studies described below.
Figure 7:
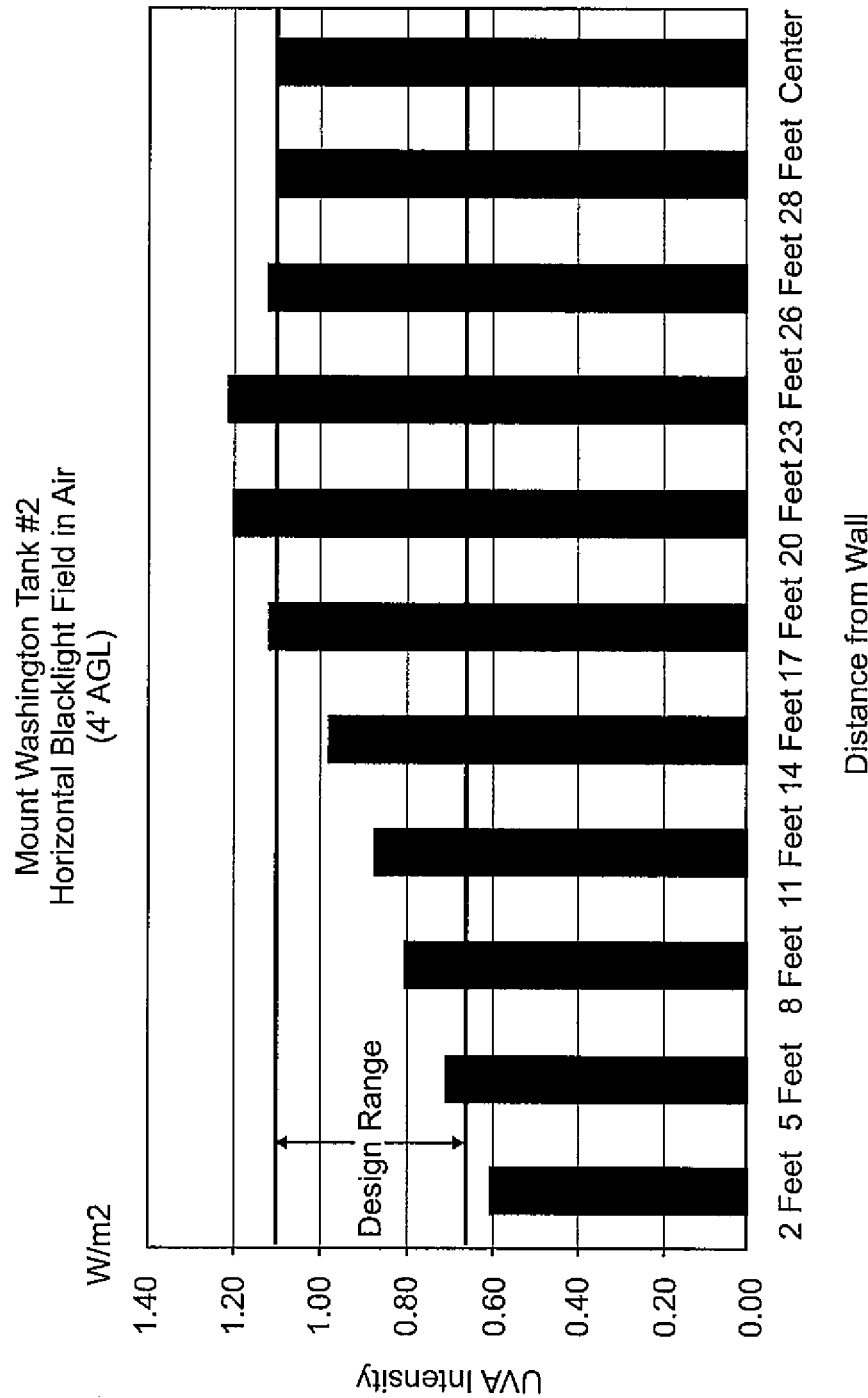
FIG. 7 is a bar graph showing UVA intensity at various points, horizontally, at 4 feet above ground level (AGL) in air in the storage tank of FIG. 6.
Figure 8:
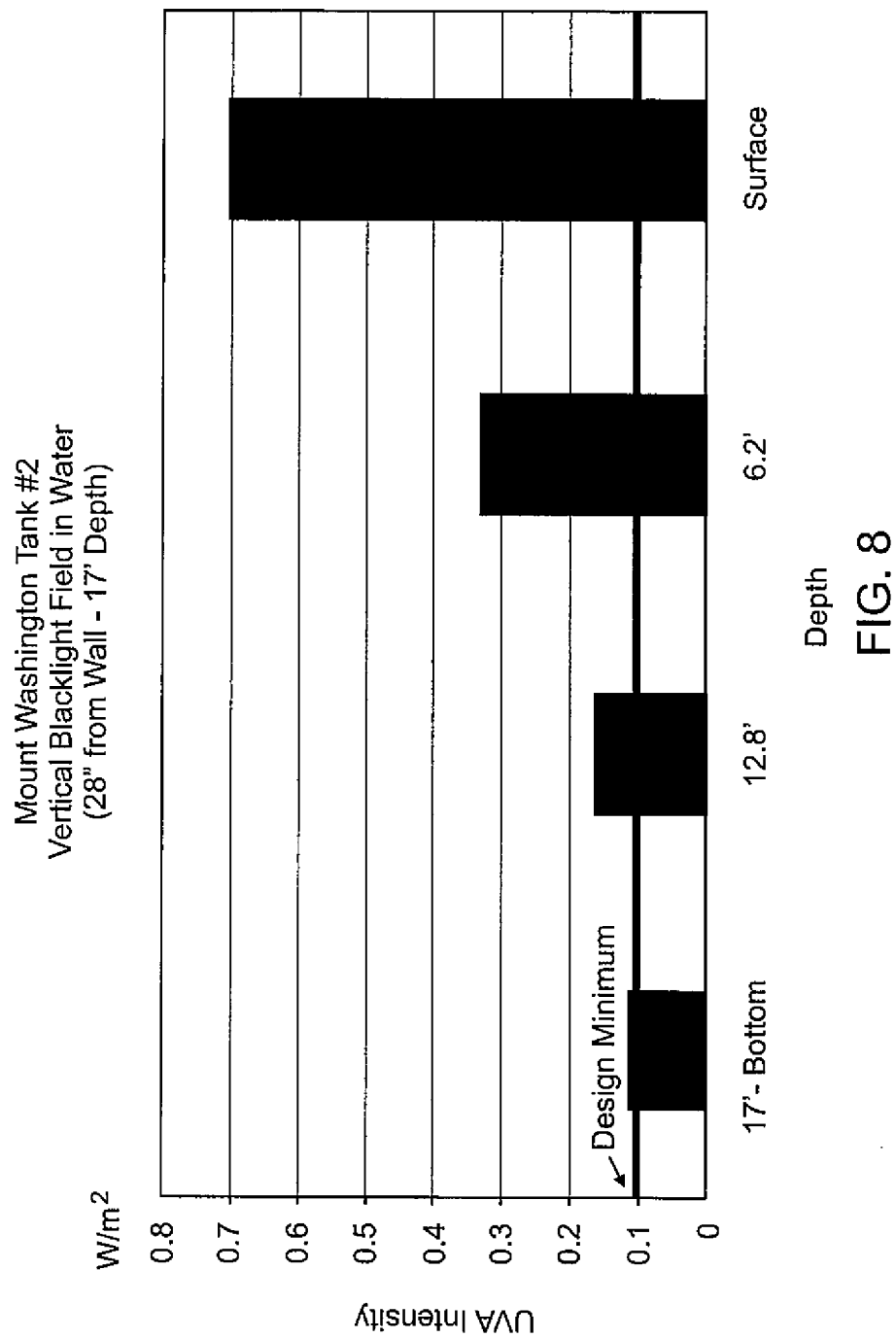
FIG. 8 is a bar graph showing UVA intensity at various points, vertically, at 28" from the wall of the storage tank of FIG. 6.
Figure 9:
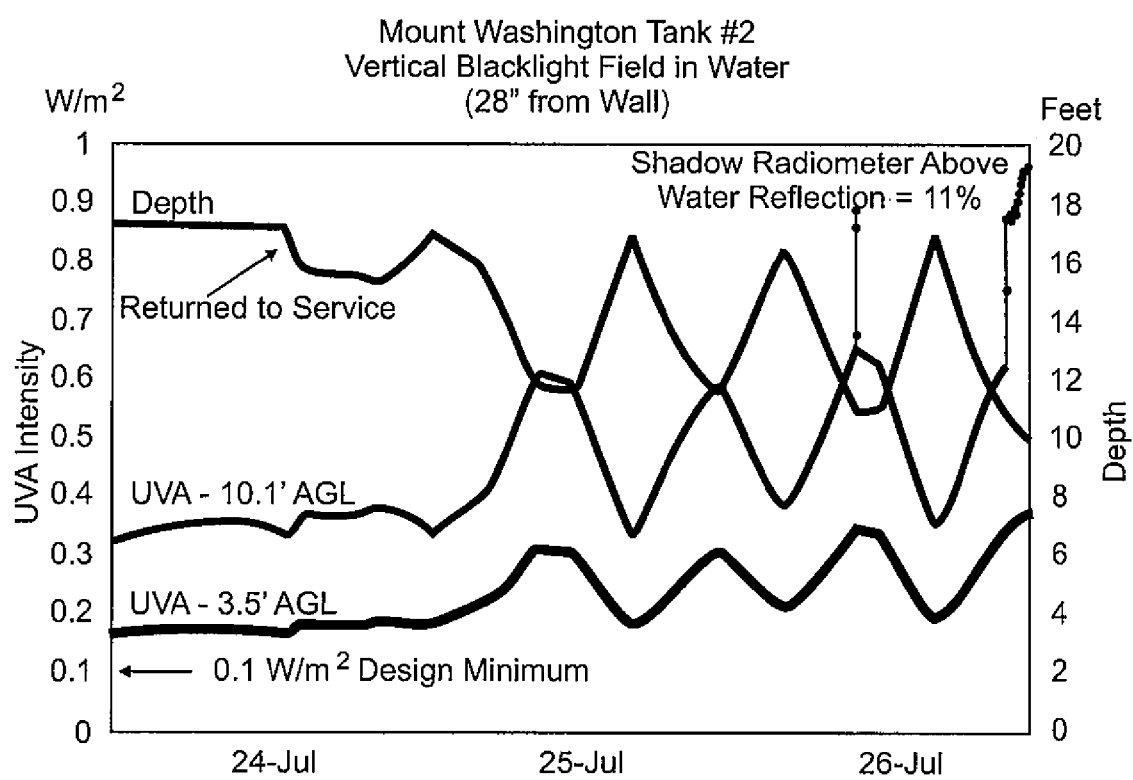
FIG. 9 is a bar graph showing UVA intensity at various points, vertically, at 28" from the wall of the storage tank of FIG. 6, over a three day period.

Referring to FIG. 6, there is shown an engineering drawing of an exemplary storage tank used in the various studies described below. FIG. 7 shows the UVA intensity at various points horizontally at 4 feet above ground level (AGL) in air in the storage tank of FIG. 6. FIG. 8 shows the UVA intensity at various points, vertically, at 28" from the wall of the storage tank of FIG. 6. FIG. 9 shows showing UVA intensity at various points, vertically, at 28" from the wall of the storage tank of FIG. 6, over a three day period.

Figure 10:
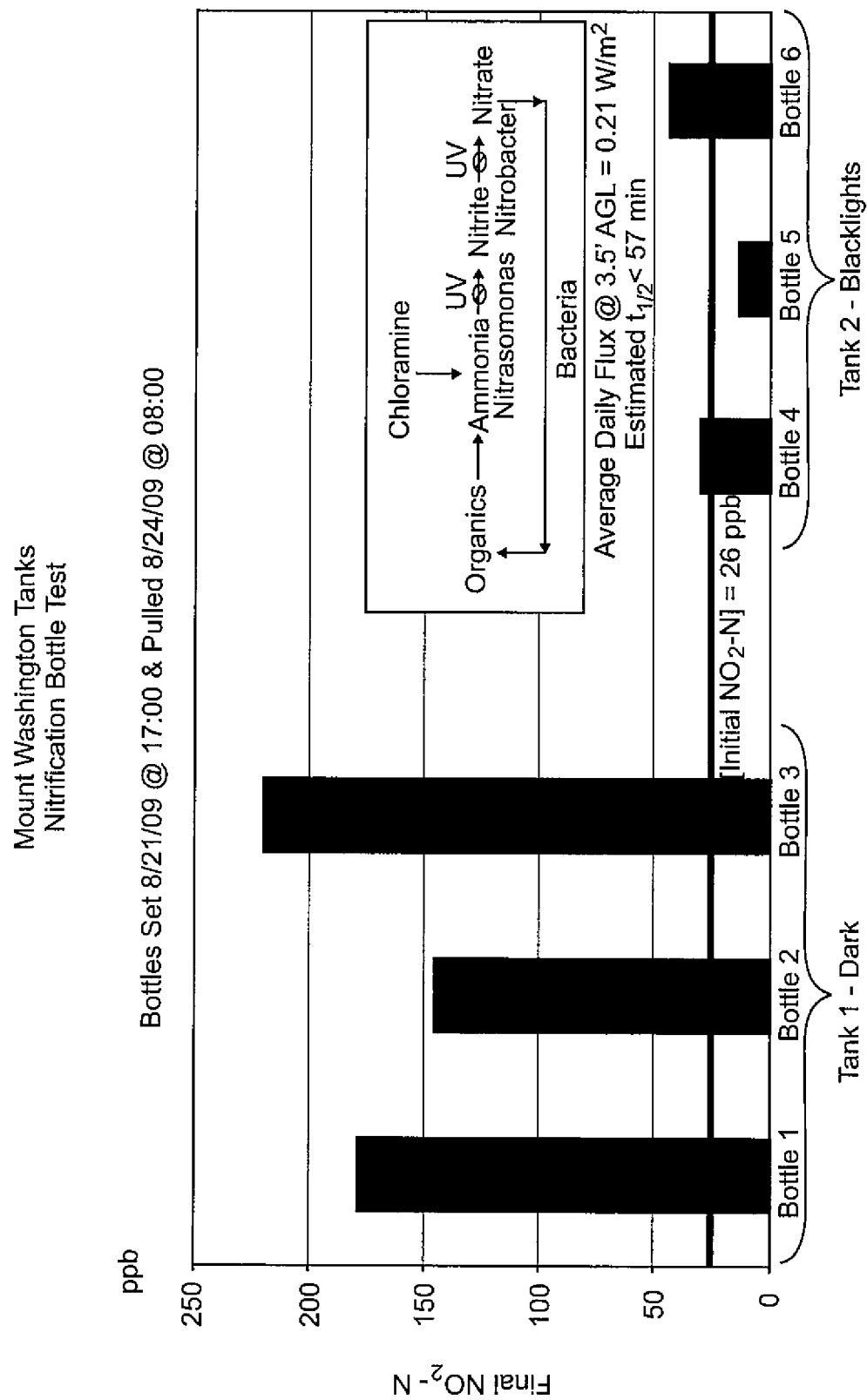
FIG. 10 is a graph describing results of a bottle test with and without the microbial nitrification photo-inhibition system of the present invention.

Referring now to FIG. 10, there is shown a graph describing results of a bottle test with and without the microbial nitrification photo-inhibition system of the present invention. In this study, three 5-liter pyrex bottles, containing 3 liters of water in each, were suspended from two water storage tanks (six 5-liter pyrex bottles in total). The bottles were placed 3.5 feet above ground level in each tank. Nitrification had begun in the water sample prior to filling the pyrex bottles. One tank was kept in the dark and one tank was provided with UVA/Visible light according to an embodiment of the present invention. As can be seen from the graph of FIG. 10, after 3 days, the tanks in the dark were of considerably poorer quality compared to those under light.

Figures 11A, 11B:
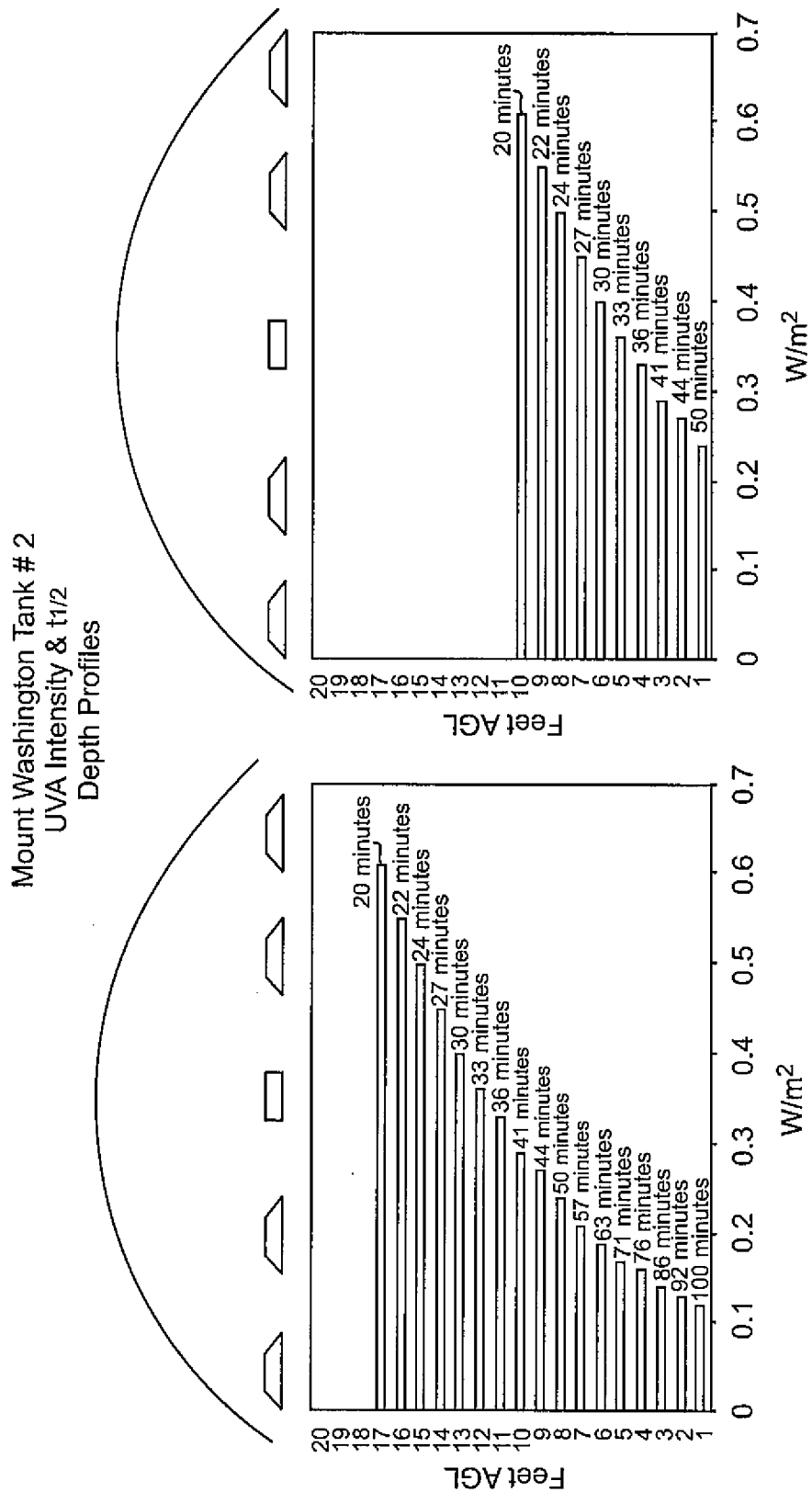
FIG. 11a is a chart describing the distribution of UVA intensity with depth at high water, including estimates of the time to half-inhibition for each flux.
FIG. 11b is a chart describing the distribution of UVA intensity with depth at low water, including estimates of the time to half-inhibition for each flux.

Referring to FIG. 11a, there is shown a chart describing the distribution of UVA intensity with depth at high water, including estimates of the time to half-inhibition for each flux. FIG. 11b shows a chart describing the distribution of UVA intensity with depth at low water, including estimates of the time to half-inhibition for each flux.

While this invention has been described in detail with particular references to exemplary embodiments thereof, the exemplary embodiments described herein are not intended to be exhaustive or to limit the scope of the invention to the exact forms disclosed. Persons skilled in the art and technology to which this invention pertains will appreciate that alterations and changes in the described structures and methods of assembly and operation can be practiced without meaningfully departing from the principles, spirit, and scope of this invention, as set forth in the following claims. Although relative terms such as "outer," "inner," "upper," "lower," "below," "above," "vertical," "horizontal" and similar terms have been used herein to describe a spatial relationship of one element to another, it is understood that these terms are intended to encompass different orientations of the various elements and components of the device in addition to the orientation depicted in the figures. In one embodiment, the method of inhibiting microbial nitrification may include each of the tasks described above, in other embodiments one or more of the tasks may be absent and/or additional tasks may be performed. Additionally, the tasks of inhibiting microbial nitrification may be performed in any suitable sequence.

What is claimed is:

1. A method of storing potable water in a drinking-water storage facility, comprising:
   containing the potable water in a covered storage tank, the potable water comprising a chloramine disinfectant having a concentration safe for human consumption; and
   illuminating the potable water with a dose of visible light from one or more lamps,
      wherein the illuminating of the potable water conserves a residual concentration of the chloramine disinfectant in the potable water by inhibiting oxidation by nitrifying microbes of ammonia in the potable water produced by degradation of the chloramine disinfectant, and
      wherein the dose of visible light has a wavelength from approximately 380 nm to approximately 430 nm.

2. The method of claim 1, further comprising mixing the water.

3. The method of claim 1, wherein the dose of visible light has an intensity of at least approximately 0.01 watts per square meter throughout the potable water.

4. The method of claim 1, wherein the illuminating of the potable water is performed for a period of approximately 24 hours.

5. The method of claim 1, wherein the one or more lamps are located above the potable water.

6. The method of claim 1, wherein the one or more lamps are submerged in the potable water.

7. The method of claim 1, wherein the one or more lamps are floating on top of the potable water.

* * * * *